US009247912B2

(12) United States Patent
Haras et al.

(10) Patent No.: US 9,247,912 B2
(45) Date of Patent: Feb. 2, 2016

(54) METHOD, IMAGE PROCESSING DEVICE AND COMPUTED TOMOGRAPHY SYSTEM FOR OBTAINING A 4D IMAGE DATA RECORD OF AN OBJECT UNDER EXAMINATION AND COMPUTER PROGRAM PRODUCT WITH PROGRAM CODE SECTIONS FOR CARRYING OUT A METHOD OF THIS KIND

(75) Inventors: Gabriel Haras, Mücke (DE); Stefan Thesen, Dormitz (DE); Carsten Thierfelder, Pinzberg (DE); Johann Uebler, Nürnberg (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 618 days.

(21) Appl. No.: 13/435,881

(22) Filed: Mar. 30, 2012

(65) Prior Publication Data

US 2012/0250820 A1 Oct. 4, 2012

(30) Foreign Application Priority Data

Mar. 31, 2011 (DE) .......................... 10 2011 006 501

(51) Int. Cl.
*A61B 6/03* (2006.01)
*A61B 6/04* (2006.01)
(Continued)

(52) U.S. Cl.
CPC ............... *A61B 6/03* (2013.01); *A61B 6/0457* (2013.01); *A61B 6/481* (2013.01); *A61B 6/486* (2013.01);
(Continued)

(58) Field of Classification Search
CPC ........ A61B 6/03; A61B 6/032; G06T 11/003; G06T 11/005; G06T 11/006; G06T 2211/40
USPC .............. 378/4, 8, 19; 382/128, 131; 600/428
See application file for complete search history.

(56) References Cited

U.S. PATENT DOCUMENTS

2009/0003513 A1 1/2009 Grass et al.
2009/0067568 A1* 3/2009 Hall et al. .......................... 378/4
(Continued)

FOREIGN PATENT DOCUMENTS

CN 101355904 A 1/2009
CN 101855652 A 10/2010
DE 102007051548 A1 6/2009

OTHER PUBLICATIONS

Flohr, Thomas, Ph.D., Cardiac CT Acquisition Modes, (Sep. 2010), Retrieved from the Internet< URL: http://usa.healthcare.siemens.com/siemens_hwem-hwem_ssxa_websites-context-root/wcm/idc/groups/public/@us/@imaging/documents/download/mdaw/ndq2/~edisp/low_dose_cardiac_ct_acquisition_modes-00308410.pdf>.*

(Continued)

*Primary Examiner* — Glen Kao
(74) *Attorney, Agent, or Firm* — Harness, Dickey & Pierce, P.L.C.

(57) ABSTRACT

A method is disclosed for obtaining a 4D image data record of an object under examination using measured data from a computed tomography system in which projection data are accepted which were acquired by way of the computed tomography system at different imaging time points by way of an helical scan method following the administration of contrast medium to the object under examination). On the basis of the projection data, image data of the object under examination are then reconstructed and linked with the imaging time points to a space/time data record. Then, a parameterized 4D image data model is individualized with adaptation to the space/time data record by varying model parameters. An image processing device and a computed tomography system with an image processing device of this kind are also described.

25 Claims, 5 Drawing Sheets

(51) Int. Cl.
  *A61B 6/00* (2006.01)
  *G06T 17/00* (2006.01)
  *A61B 5/0456* (2006.01)
  *A61B 5/00* (2006.01)

(52) U.S. Cl.
  CPC .................. *A61B 6/503* (2013.01); *A61B 6/507* (2013.01); *G06T 17/00* (2013.01); *A61B 5/0456* (2013.01); *A61B 5/7207* (2013.01); *A61B 6/541* (2013.01); *G06T 2200/08* (2013.01); *G06T 2210/41* (2013.01)

(56) References Cited

U.S. PATENT DOCUMENTS

| | | |
|---|---|---|
| 2009/0123050 A1 | 5/2009 | Ionasec et al. |
| 2009/0124892 A1 | 5/2009 | Bruder et al. |
| 2009/0141855 A1 | 6/2009 | Bruder et al. |
| 2010/0266182 A1 | 10/2010 | Grass et al. |
| 2011/0060576 A1 | 3/2011 | Sharma et al. |

OTHER PUBLICATIONS

"Flash Speed. Lowest Dose. SOMATOM Definition Flash", SIEMENS AG brochure, URL: http://medical.siemens.com/siemens/it_IT/gg_ct_FBAs/files/brochures/CT_Definition_Flash.pdf, Nov. 2010, Munich, Germany.

German priority document application No. DE 10 2011 006 501.6 filed Mar. 31, 2011 and published on Oct. 4, 2012.

Chinese Office Action dated Dec. 15, 2014 for corresponding Chinese Application No. 201210066142X.

German Office Action dated Jan. 26, 2015 for corresponding German Application No. 102011006501.6.

* cited by examiner

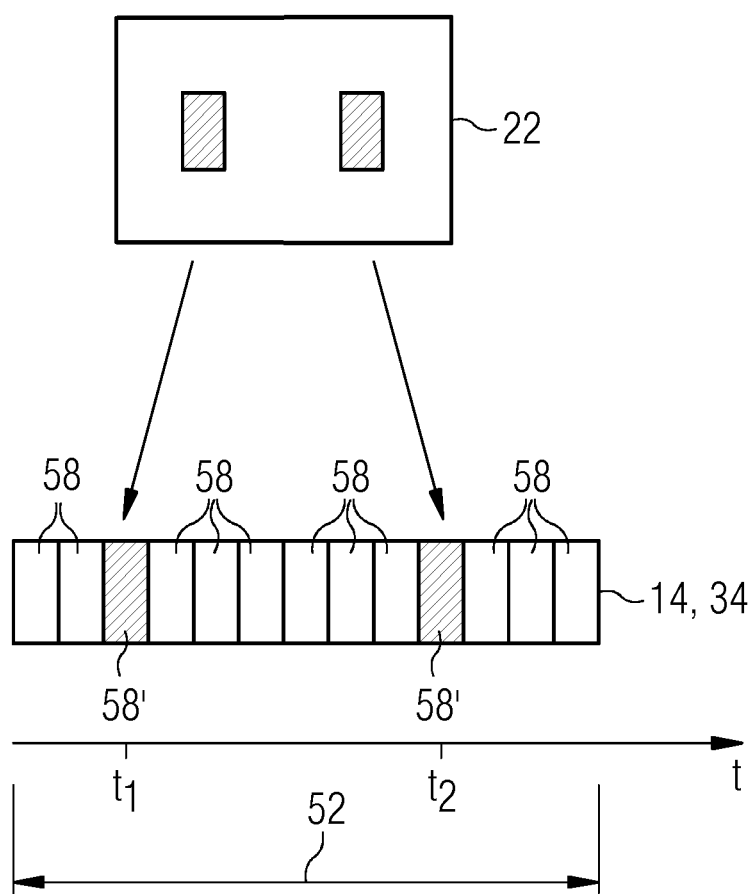

METHOD, IMAGE PROCESSING DEVICE AND COMPUTED TOMOGRAPHY SYSTEM FOR OBTAINING A 4D IMAGE DATA RECORD OF AN OBJECT UNDER EXAMINATION AND COMPUTER PROGRAM PRODUCT WITH PROGRAM CODE SECTIONS FOR CARRYING OUT A METHOD OF THIS KIND

PRIORITY STATEMENT

The present application hereby claims priority under 35 U.S.C. §119 to German patent application number DE 10 2011 006 501.6 filed Mar. 31, 2011, the entire contents of which are hereby incorporated herein by reference.

FIELD

At least one embodiment of the invention generally relates to a method and/or an image processing device for obtaining a 4D image data record of an object under examination using measured data from a computed tomography system and a computed tomography system with an image processing device of this kind. At least one embodiment of the invention also generally relates to a computer program product with program code sections for carrying out at least one embodiment of the method.

BACKGROUND

With the aid of computed tomography (CT), suitable measuring and evaluation methods can be used to provide information on the essential relevant diagnostic parameters of an examined organ, in particular a heart. In particular in the case of examinations in the region of the heart, it is important that as many clinically relevant parameters as possible are acquired with high precision and little stress on the patient, i.e. the lowest possible X-ray dose and quantity of contrast medium.

During heart examinations, computed tomography is currently mainly used to perform the following main evaluations, which generally require a plurality of very different measurements to be performed:

1. Detection and evaluation of calcification in coronary vessels, on cardiac valves and the aorta. Here, usually a simple measurement of the cardiac region is sufficient, i.e. a single scan covering the cardiac region without any contrast medium.
2. Analysis of the coronary vessels for the diagnosis of coronary heart disease. According the current state of the art, for this the heart is recorded by way of plurality of measurements at different time points of the heartbeat (i.e. in different cardiac phases). The dose required for this currently lies in the region of 5 to 10 mSv. The data are then usually analyzed slice by slice in that the inner and outer contours of the cardiac muscle of the left and/or right ventricle are determined automatically or interactively.
3. Functional analyses of the heart, such as, for example, spatial and temporal analysis of the left and right ventricles to determine the shape and volume change of the myocardium and myocardial mass and ejection fraction. Nowadays, this is usually done by taking a so-called multiphase scan, wherein for a kinetic analysis of the heart, generally virtually the entire cardiac cycle is determined as a four-dimensional volume. This means a 4D image data record is generated containing three-dimensional spatial image data at different time points or movement phases, which ultimately corresponds to a sort of film of the motion of the heart.
4. Perfusion measurements to investigate the blood supply to the cardiac muscle and for determining diagnostic parameters relating to the blood volume and blood flow. For this, different contrast medium images are produced, optionally also at different time points of the passage of the contrast medium. With many methods, time-resolved measurements of the heart volume are also performed, i.e. once again a type of 4D image data record is recorded.

More modern high-end computed tomography systems use helical scan methods with a particularly high pitch, which enable the acquisition of images of the heart in a so-called "flash mode". Acquisition in "flash mode" is frequently performed using a dual-source-computed tomography system with a movable patient's bench moving at speeds of, for example 40 cm/s, during the recording. This enables a heart (measuring about 15 cm in direction of movement of the patient's bench) to be scanned in about 200 to 250 ms. This enables a complete 3D image to be taken in a single movement phase of the heart, which can result in a significant reduction in the dose compared to earlier methods. However, this "flash mode" only provides a snapshot in a type of "still image" of the heart and therefore does not permit a functional analysis of the heart. For this, as before, it is necessary to produce a whole series of sequential images or EKG-triggered whole images of the heart. However, this results in a correspondingly higher exposure to radiation.

SUMMARY

At least one embodiment of the invention provides a method, an image data processing system and/or a computed tomography system with which a 4D image data record can be generated for a functional analysis with reduced radiation exposure for the object under examination.

With the method according to at least one embodiment of the invention for obtaining a 4D image data record of an object under examination using measured data from a computed tomography system, projection data are accepted, which were acquired by way of the computed tomography system at different imaging time points by way of a helical scan method. Here, the projection data acquired by way of the computed tomography system can, for example, be available in stored form from a measurement performed previously and are loaded from the memory for carrying out at least one embodiment of the method for example by an image processing device according to at least one embodiment of the invention. Alternatively, the measurement of the projections can be performed using the computed tomography system itself according to the method according to at least one embodiment of the invention for obtaining a 4D image data record of an object under examination.

An image processing device according to at least one embodiment of the invention should, on the one hand, comprise an interface for accepting projection data of an object under examination, which were acquired by way of a computed tomography system at different imaging time points by way of a helical scan and for accepting time data containing information on the imaging time points belonging to the projection data.

The image processing device also comprises a reconstruction device in order to reconstruct image data of the object under on the basis of the projection data and link them with the imaging time points to a space/time data record; a model interface to accept a prespecified parameterized 4D image data model; and a model individualization device in order, the generation of the individualized 4D image data record, to individualize the 4D image data model with adaptation to the space/time data record by varying model parameters.

An image processing device of at least one embodiment can be part of a computed tomography system, i.e. it can, for example, be installed on a control and evaluation computer in the computed tomography system. Correspondingly, at least one embodiment of the invention also includes an X-ray computed tomography system with at least one X-ray source and at least one detector for the acquisition of projection data records for an object under examination and with an image processing device of this kind.

At least one embodiment of the invention is further directed to a computer program product, which may be loaded directly into a memory of an image processing device and/or a computed tomography system, with program code sections, to carry out all the steps of at least one embodiment of the method according when the program is executed in the image processing device and/or the computed tomography system.

BRIEF DESCRIPTION OF THE DRAWINGS

The invention is described again in more detail below with reference to the attached diagrams using example embodiments. Here, in the different diagrams the same components have been given identical reference numbers. The diagrams show.

Figure 1:
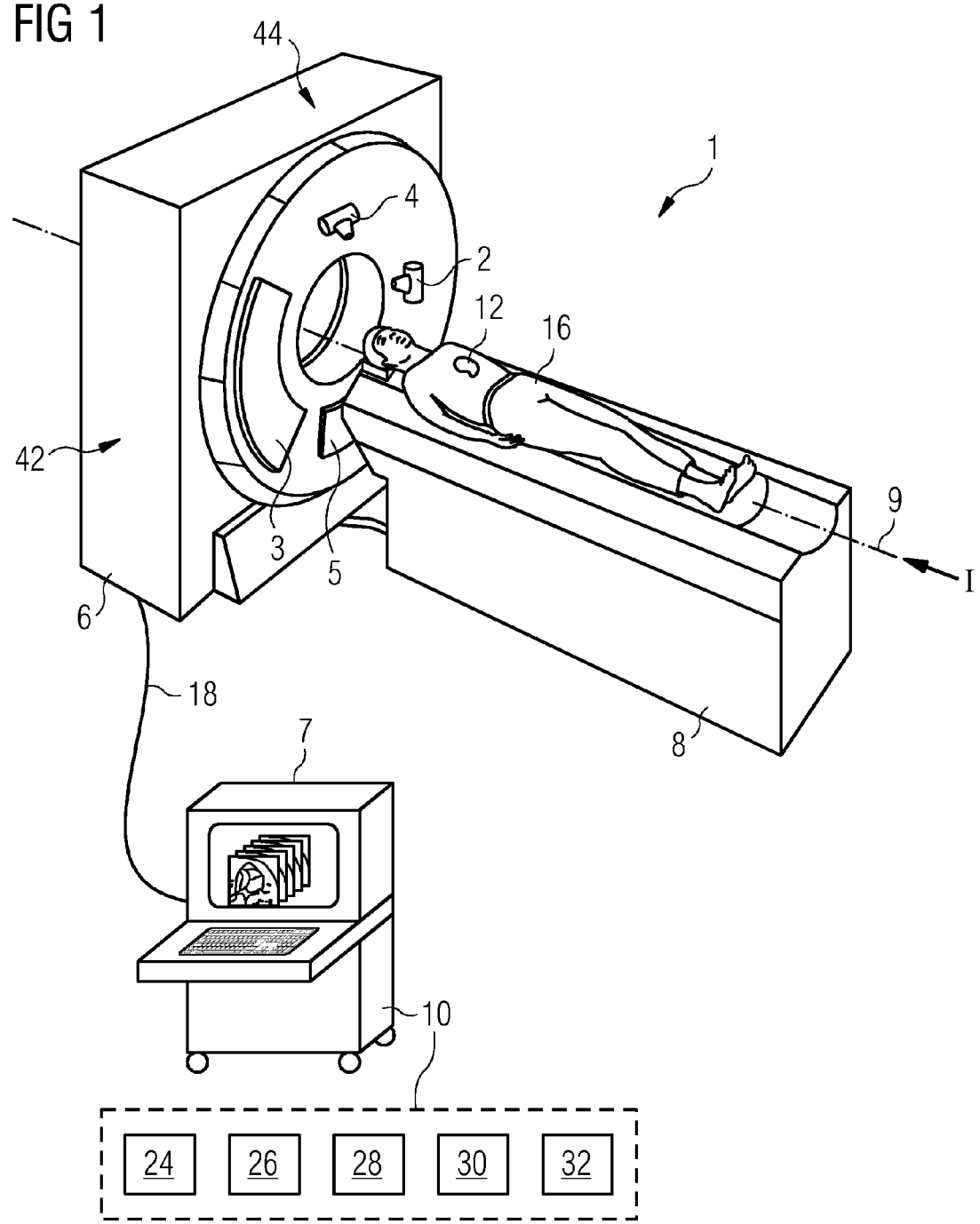
FIG. 1 a schematic representation of an example embodiment of a computed tomography system according to the invention with an image processing device, FIG. 2 a schematic representation of an EKG, FIG. 3 a speed profile of the patient's bench, FIG. 4 a flowchart for obtaining projection data, FIG. 5 a flowchart of an example embodiment of the method according to the invention, and FIG. 6 a schematic representation for individualizing a 4D image data model.

The invention will now be explained in greater detail on the basis of different example embodiments described in conjunction with the drawings.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

With the method according to at least one embodiment of the invention for obtaining a 4D image data record of an object under examination using measured data from a computed tomography system, projection data are accepted, which were acquired by way of the computed tomography system at different imaging time points by way of a helical scan method. Here, the projection data acquired by way of the computed tomography system can, for example, be available in stored form from a measurement performed previously and are loaded from the memory for carrying out at least one embodiment of the method for example by an image processing device according to at least one embodiment of the invention. Alternatively, the measurement of the projections can be performed using the computed tomography system itself according to the method according to at least one embodiment of the invention for obtaining a 4D image data record of an object under examination.

With a helical scan-method (often also called "spiral-scan"), the X-ray tube belonging to the computed tomography system and—depending upon the design also the detector—revolve round the object under examination in a helical or spiral shape. This means that, during the recording of the projection data, the X-ray tube and possibly the detector rotate about an axis of rotation around the object under examination and, at the same time, the object under examination is moved along the axis of rotation in a transversal feed direction relative to the X-ray tube and detector.

The projection data are then used to reconstruct image data of the object under examination in a known manner, for example by a conventional back projection. Corresponding to the projections, which were in fact measured at different imaging time points, these image data also show the object under examination at different times or imaging time points. On closer examination, these image data can be seen as thin slices of the object under examination showing the object under examination in the respective slice at a specific time or in a very short time interval in which the projections, which were used for the reconstruction of the slice in question, were measured.

The reconstructed image data of the object under examination are then linked with their imaging time points to a space/time data record. The space/time data record is, therefore, resolved spatially and temporally, i.e., in addition to the actual spatial image data (also called "geometric data"), it also contains information on the time point at which these image data were recorded, wherein here, for example, exactly one time point can also be assumed to be representative of a short time interval in which the projections for the respective image data were measured. Here, the space/time data record can be a complete 4D image data record containing the full spatial 3D image information (i.e. volume image data) plus the time information, or a data record containing spatial 2D image data (that is, for example, individual slice images) and their position relative to each other plus information on the recording time.

The linkage of the image data with the imaging time points to a space/time data record can take place by the formation of a new data record in which, in a specific data format, the spatial image data and the information on the imaging time points can be entered assigned to each other. Here, an example is once again a type of 3D film. Alternatively, the space/time data record can also be formed with the aid of indicators, which, refer, for example from files with the geometric data, to the time data or vice versa.

This space/time data record is used in a further step to individualize a parameterized 4D image data model by varying model parameters. Here, the 4D image data model is a type of "normal film", which, was for example determined from a plurality of corresponding measurements on patients or test subjects. Here, "parameterized" means that the 4D image data model has certain variable parameters by which the 4D image data model can be changed. Hence, this is a generalized, but variably adaptable model of a normalized movement pattern of a "normal object under examination". The movement pattern can, for example, be the cardiac cycle of a beating heart. The variable parameters of the 4D image data models can, on the one hand, be spatial parameters, such as, for example, specific dimensions or other shape parameters of the object under examination (in the case of a heart. for example, the entire length of the heart, the dimensions of the ventricles of the heart, the thickness of the walls of the ventricles of the heart etc.), or also temporal parameters, which relate to the movement pattern. Here, a parameterized 4D image data model of this kind generally has a plurality of variable parameters of this kind, for example up to 50 parameters.

Since the 4D image data model in generalized form reproduces the movements of the object under examination, the image data obtained for the different imaging time points can be used as support points in order to optimize the variable parameters of the 4D image data models in such a way that the 4D image data model is adapted as well as possible to these image data and the associated time points. The result is then an individual 4D image data record, which reproduces a spatial image of the object under examination during a movement pattern.

Hence, at least one embodiment of the method enables a reduction of the radiation exposure, since, to obtain the 4D image data record, it is only necessary to perform measurements at very few selected imaging time points measurements relative to the total length of the movement cycle, wherein the imaging time points preferably lie in only a few, for example one to four, preferably two, shorter measuring periods relative to the total length of the movement cycle. The recording of projection data only at the imaging time points means it is not necessary to perform a complete measurement of the entire movement phase of the object under examination to be able to carry out a functional analysis of the object under examination and this reduces radiation exposure. For example, it is now sufficient to use a dose-optimized helical scan, in particular a scan in the aforementioned "flash mode", to produce in each case a rapid "still image" in a systolic and a diastolic phase of a heart in order to determine sufficient information therefrom for an evaluation of the complete movement cycle.

Preferably, therefore, a 4D image data record determined with a method of this kind is used in a method according to at least one embodiment of the invention to determine structural and/or functional data of an object under examination, particularly preferably a heart, in that this 4D image data record is analyzed with respect to the desired structural and/or functional data. The structural and/or functional data preferably analyzed according to this method include, on the one hand, functional information, such as, with a heart, the determination of the ejection fraction, but, on the other hand, also perfusion measurements. Precisely which structural and/or functional data are obtained by way of the 4D image data depends on which cardiac phases were determined, the conditions under which the measurements were performed, that is, for example, with or without contrast medium, at which time point of the administration of the contrast medium and, if applicable, which further image data records are available, for example whether, in addition to a contrast medium measurement, there is also a plain comparative measurement or whether possibly a dual-energy measurement was performed. Different possibilities will be explained later.

An image processing device according to at least one embodiment of the invention comprises an interface for accepting projection data of an object under examination, which were acquired by way of a computed tomography system in the manner described above and for accepting time data containing information on the imaging time points belonging to the projection data. Here, an interface of this kind can also be implemented by two separate partial interfaces, for example a projection data interface to the scanner and a time data interface with a time-measuring device, a clock-pulse generator or the like, for example an EKG during a heart examination.

The image processing device also comprises a reconstruction device in order to reconstruct image data of the object under on the basis of the projection data and link them with the imaging time points to a space/time data record. This can, for example, be a conventional reconstruction unit, which is additionally suitably equipped or coupled to a separate linking unit in order to link the image data with the time data.

Also included is a model interface to accept a prespecified parameterized 4D image data model. This can be an interface to a simple memory in which the 4D image data model is stored. However, in principle, it is also possible to store several different 4D image data models in a memory of this kind and for the image processing unit additionally to comprise a selecting unit (for example using a user interface) for selecting a 4D image data model. For example, although in principle to obtain the individualized 4D image data record, a single 4D image data model can be sufficient for all objects under examination of a specific type, such as, for example, a human heart, a much quicker, possibly ultimately even better adaptation of the 4D image data models to a measured space/time data record can be achieved in that, for example, the current 4D image data model is selected from a plurality of patient-specific 4D image data models. The different 4D image data models can, for example, be customized for male and female patients. It is also possible for 4D image data models to be available for selection which are also customized, for example, for children, adolescents, adults or graded in some other way according to age levels. It is also possible for different 4D image data models to be provided for different typical clinical pictures. The selection of a suitable 4D image data model can here be performed automatically, for example on the basis of data from an electronic patient record, or by a user.

Finally, an image processing device according to at least one embodiment of the invention includes a model individualization device in order, for the generation of the individualized 4D image data record, to individualize the 4D image data model with adaptation to the space/time data record by varying model parameters.

An image processing device of at least one embodiment can be part of a computed tomography system, i.e. it can, for example, be installed on a control and evaluation computer in the computed tomography system. Correspondingly, at least one embodiment of the invention also includes an X-ray computed tomography system with at least one X-ray source and at least one detector for the acquisition of projection data records for an object under examination and with an image processing device of this kind. However, in principle, an image processing device of this kind can also be implemented as an independent computer unit or on another computer unit, which is connected, for example, to an X-ray system via a network for data acceptance and can be supplied in another way with corresponding data.

In particular, the reconstruction device, possibly the linking unit and the model individualization device can each be implemented as software modules on a suitable computer with corresponding memory capabilities. It is also possible for an interface to be implemented, for example, in the form of pure software if it is possible to accept the data from other program units. In principle, however, the interface can also be implemented as a combined hardware/software interface in order to implement an external input, for example with the aid of software components with specially configured hardware interfaces. Insofar, at least one embodiment of the invention includes a computer program product, which can be loaded directly into a memory of a computer of the image processing device and/or a computed tomography system, with program code sections in order to carry out all the steps of the method according to at least one embodiment of the invention.

The dependent claims and the further description contain particularly advantage embodiments and further developments of the invention, wherein in particular the claims of one category can also be further developed in analogy with the claims of another category.

The object under examination can in principle be a body of a living being or a body part thereof. The body part can in particular be an organ, such as, for example, the heart, the lungs, the intestine etc., of a living being or also only a part of an organ or a functional organism, such as, for example, specific regions of blood vessels or a section of an intestine.

At least one embodiment of the method can advantageously be used to obtain a 4D image data record with any moving objects. The movements can be peristaltic movements, such as swallowing or bowel movements. However, preferably at least one embodiment of the method is used with objects under examination which move cyclically, i.e. which (more or less regularly) periodically pass through a defined movement cycle. The object under examination can therefore also be a lung, for example, which performs breathing movements during the acquisition of the projection data. As already mentioned above, it is particularly advantageous to use at least one embodiment of the method for data acquisition on a beating heart.

The imaging time points are preferably defined with reference to the movement, for example, in the case of a cyclic movement referred to a specific reference time point in the movement cycle. In the case of data acquisition on a heart, for example, a reference time point can be defined by the R wave in the EKG of the heart.

Preferably, projection data are acquired in at least two temporally spaced apart acquisition periods. This means that the two acquisition periods are separated from each other by a pause in which the computed tomography system in some circumstances does not acquire any projection data. Therefore, the imaging time points are selected so that at least a part of the imaging time points have a large temporal spacing compared to the total length of the movement. This results in a better adaptation of the 4D image data models to the space/time data record with only a relatively few support points, i.e. only a small amount of data in the space/time data record.

Particularly preferably, the different imaging time points are here established in such a way that they encompass a plurality of spaced-apart time points within at least two different movement phases of the object under examination in the movement cycle. In the case of a heart, these can preferably be the systolic phase and the diastolic phase. Since the heart movement is relatively low in the diastolic phase, the acquisition of projection data during the diastolic phase results in an acquisition with small motion artifacts. Here, the data acquisition in the different movement phases can take place in separate measurements or scans. I.e. with heart imaging, for example, a first measurement is performed, with which an image data record is obtained during the diastolic phase, and a second measurement is performed with which an image data record is obtained during the systolic phase. Here, it is in principle possible to acquire projection data both initially during the diastolic phase and then during the systolic phase or, alternatively, initially during the systolic phase and then during the diastolic phase. Preferably, no projection data is acquired in the interim period. This again significantly reduces the radiation exposure of the object under examination.

The acquisition of the projection data over different imaging time points can encompass a plurality of movement cycles of the object under examination. This means that a first imaging time point lies within a first execution of the movement cycle of the object under examination, while a second imaging time point lies within a second execution of the movement cycle of the object under examination. This can result in imaging errors since the position of the object under examination can change between two movement cycles. Therefore, preferably the projection data acquired at different imaging time points, which are acquired within a movement phase, are also acquired within a movement cycle. Therefore, if, for example, projections of a heart are acquired in two different movement phases, it is preferably attempted to make the measurement at least fast enough for a complete acquisition of the heart to be completed in each case in one of the phases within a cardiac cycle. This makes the probability of the occurrence of disruptive motion artifacts correspondingly low.

As already mentioned, it is, in principle, also possible to use a computed tomography system with only one X-ray source and one detector system. However, preferably—in particular in view of the preferred rapid acquisition of the projections—for the purposes of at least one embodiment of the invention, a computed tomography system with at least two X-ray tubes, that is, for example, a dual-source CT, is used. A dual-source CT of this kind usually comprises two X-ray tubes with an angular offset of 90°, which are arranged on a gantry and hence are rotatable about a common axis. A computed tomography system of this kind permits more rapid acquisition of the projection data required for a complete reconstruction since the two X-ray tubes with corresponding assigned detector systems enable the simultaneous acquisition of different projections of the object under examination. This can result in virtually a halving of the measuring time. On close examination, with a helical scan, the two X-ray tubes describe the trajectories of two intertwined helices or spirals.

Here, if only an acceleration of the measuring time is concerned, the two X-ray tubes are operated with the same X-ray voltage. Alternatively, the two X-ray tubes can be operated with different X-ray voltages in order to carry out a dual-energy-measurement. In a dual-energy-measurement of this kind, image data with different X-ray energies or X-ray spectra are generated. Since the attenuation of most materials is dependent upon the X-ray, it is additionally possible for a contrast-enhanced image and a plain image to be calculated from the image data obtained in this way and then used for further evaluation, for example of the heart. However, a dual-energy measurement of this kind requires a longer measuring time than is the case when the two X-ray sources are used to compile common image data with only one X-ray energy.

During a helical scan, the object under examination is moved on a patient's bench relative to the projection imaging system, i.e. the X-ray tube or the X-ray tubes and the associated detectors. In this context, "relative" means that the bench is moved in space with a fixed projection imaging system, or vice versa the projection imaging system is moved relative to the bench or that both components are moved relative to each other. Since, with the majority of systems, it is the bench which is moved, in the following—unless stated otherwise, without restriction to this variant—it will also be assumed, by way of example only, that it is the bench which is moved and that the projection imaging system is fixed or only rotates about the feed device.

Particularly preferably, the movement of the patient's bench is controlled in dependence on an EKG signal from a patient or test subject to be examined or the heart thereof. The use of an EKG signal to control the movement of the patient's bench enables it to be ensured that an imaging time point lies in a specific movement phase, for example in the systolic or diastolic phase, wherein obviously the projection imaging system, i.e. the X-ray tube(s) and the detector system also have to be suitably triggered. The reference time point, or trigger time point, used can, for example, be the R wave of the EKG.

In order then to be able to perform a recording of a heart in about 200 to 250 ms, during the acquisition of the projection data, the patient's bench is preferably at least temporarily moved at a feed rate of up to 45 cm/s or more. This so-to-speak enables the recording of still images in the diastolic phase and the systolic phase of the heart.

The direction of movement of the patient's bench can be same during the recording of the two phases. To this end, at the end of the measurement of, for example, the systolic phase, the direction of movement of the patient's bench is initially reversed and the patient's bench returned back into its initial position. This is then repeated in the diastolic phase of the heart. As a result, the imaging time points of the different movement phases lie in different cardiac cycles. In addition, the return of the patient's bench into the initial position prolongs the total length of the measuring process unnecessarily and this encourages the formation of motion artifacts, for example due to movements of the patient/test subject between the individual recordings. Preferably, therefore, the direction of movement of the patient's bench is reversed between a recording of projection data in a first and a second movement phase, particularly preferably during one movement cycle. This means that the direction of movement of the patient's bench is reversed after the first recording in the first movement phase and immediately after this, during a return of the table opposite to the direction of movement during the first recording, the recording in the second movement phase takes place. This can significantly reduce the overall measuring time since no time is required to return to the initial position of the patient's bench. In particular, in this way, during heart imaging, with optimization of the table movement and the use of particularly fast measuring methods, such as the "flash mode", images in the systolic phase and in the diastolic phase can be recorded very quickly one after the other, for example in a time window of only 6 s.

One parameter which exerts an influence on the time required to acquire a projection data record for the reconstruction of image data for a specific volume during a helical scan method is the so-called "pitch". The pitch is defined as the quotient of the feed distance covered (normalized to the detector width in the z direction, i.e. in the feed direction) per each complete circulation of the X-ray source or of the projection imaging system. One limiting variable is the detector width in the feed direction. In order, for example, to acquire a volume with a field of view of 50 cm with no gaps at the measuring edge, the maximum possible pitch is 1.5, which is to say the feed (in detector width) in the z direction does not exceed 1.5 times the detector width. In order, when using the method according to at least one embodiment of the invention, for example, to acquire the complete heart during a cardiac phase, preferably a value of at least 3 is selected for the pitch, particularly preferably a pitch of up to 3.5 can be selected. In addition to shortening the measuring time for the acquisition of the projection data and hence reducing the radiation exposure, a pitch as high as this in also reduces the negative influence of motion artifacts on the image quality.

The acquisition of projection data can take place with variable speeds of the patient's bench. However, preferably, before commencing the acquisition of the projection data, the patient's bench is accelerated during an acceleration phase to a measuring velocity. This ensures that, during the acquisition of the projection data, the patient's bench, i.e. in particular at the imaging time points, is moved with a defined constant measuring velocity, preferably, for example, of 40 cm/s, and the quality of the image data is not negatively influenced by fluctuations in the feed rate.

The example embodiment of a computed tomography system 1 shown in FIG. 1 is a dual source computed tomography scanner 1. This comprises a gantry (not shown) housed in a gantry housing 6 on which two tube/detector systems 42, 44 are mounted with an angular offset of 90°, each of which is formed from an X-ray tube 2, 4 and an opposite detector 3, 5. The gantry with the X-ray tubes 2, 4 and the detectors 3, 5 rotates about a system axis 9 during a recording of projection data. Here, the object under examination 12 is the heart 12 of a patient 16. The patient 16 is located on a patient's bench 8 that can be moved along the system axis 9 and in this way, during the examination, can be pushed along the system axis through the measuring field acquired by the tube/detector systems 42, 44. Here, the patient's bench 8 can be moved in and against the direction I. The dual source computed tomography scanner 1 is designed so that the patient's bench 8 can be moved with a pitch of up to 3.5. For the purposes of the method according to at least one embodiment of the invention, the measurement is performed with a helical scan method, i.e. the table is moved simultaneously during the circulation of the tube/detector systems 42, 44 and the acquisition of projection data.

The control of the dual source computed tomography scanners 1 and, possibly, the image processing and the method for obtaining a 4D image data record can be performed by a conventional control device 7. Therefore, here this control device 7 additionally comprises an image processing device 10 designed according to at least one embodiment of the invention. The image processing device 10, in particular the components of the image processing device 10 described below, can here also be implemented at least partially in the form of software modules on one or more interworking processors with corresponding memories. Here, it is also possible to use memories and processors which would otherwise be used by the control device 7 for other tasks, for example the control.

The image processing device 10 here comprises an interface 24 for accepting the projection data 18 of the heart 12 acquired by the detectors 3, 5 during a helical scan method at different imaging time points. This interface 24 also accepts time data, which contains information on the imaging time points t1, t2 belonging to the projection data 18. These time data can actually be sent with the projection data in a data format. However, they can also be accepted by a separate device, for example an EKG device (not shown) connected to the patient 16.

The image processing device 10 also comprises a reconstruction device 26 for reconstructing three-dimensional image data 20 of the object under examination 12 on the basis of the projection data 18. This can be a conventional reconstruction device. This only has to be embodied or modified so that it is able to link the reconstructed image data with the imaging time points t1, t2 to a space/time data record 22 and store them in a suitable data format.

This can, on the one hand, take place in that the reconstruction unit continuously assigns the image data to the respective time points during the reconstruction. Alternatively, the reconstruction device can also initially reconstruct a complete three-dimensional image data volume from the projection data of the helical scans and then dissect the image data, then for example in a dissection unit, into individual slice images according to their imaging time points and position and then assign the slice images to the time data in a space/time data record in an assignment unit. The dissection unit and the assignment unit (neither shown) can, for example, also be implemented in the form of suitable software, also as part of a modified reconstruction unit.

The image processing device 10 also has a model interface 28 for accepting a prespecified parameterized 4D image data model 34. For this, a number of different 4D image data models can be stored can in a memory (not shown) and a selection unit in the model interface 28 is used to select a suitable 4D image data model for the current examination.

A model individualization device 30 is then used to adapt the 4D image data model 34 to the space/time data record 22 by varying model parameters. Conventional adaptation methods or fit methods can be used for this, for example optimization methods with the aim of minimizing a mean quadratic deviation between specific points of the space/time data record 22 and of the 4D image data model 34. In this way, the 4D image data model 34 is individualized or an individual 4D image data record 14 is generated which very accurately reproduces the actual processes and geometries in the specific object under examination, in the present case, for example,
the exact movement of the heart, the maximum and minimum extension of the ventricles of the heart, the movement of the cardiac valves, the change in the thickness of the cardiac walls etc., during a movement cycle.

Then, as will be explained later, the individual 4D image data record 14 is analyzed with respect to specific parameters such as, for example, the aforementioned maximum and minimum expansion of the ventricles of the heart, the change in the thickness of the cardiac walls etc., in an analysis unit 32 of the image processing device 10. Here, the data are, for example, processed for an analyst and output in a desired representation, for example a polar plot.

Reference is made at this point to the fact that the computed tomography system 1 and in particular the control device 7 with the image processing device 10 can also be embodied differently and, above all, can also comprise further components other than those described above. For example, the control device 7 can further comprise one or more memory units, in which, for example, the projection data, image data reconstructed therefrom, individualized 4D-image data records etc. can be stored. The control device 7 can also be connected via a suitable interface to a network (not shown) via which data can be accepted and sent, for example to accept 4D image data models and transmit finally reconstructed image data and individualized 4D-image data records to bulk storage systems, diagnostic stations.

Figure 2:
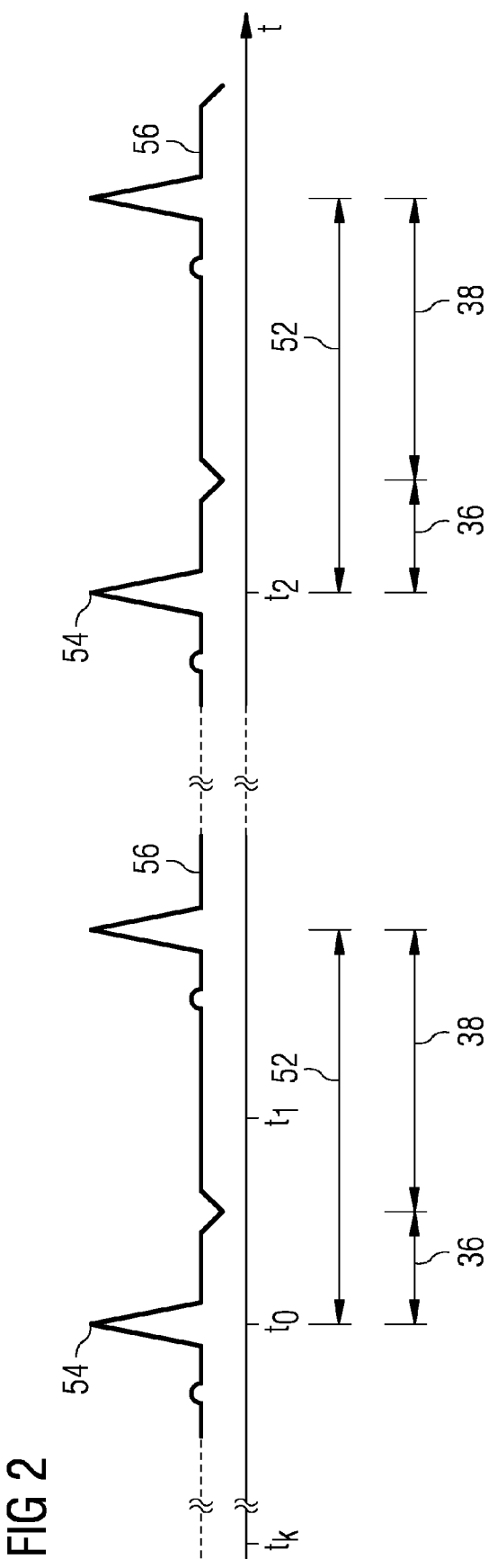
Figure 3:
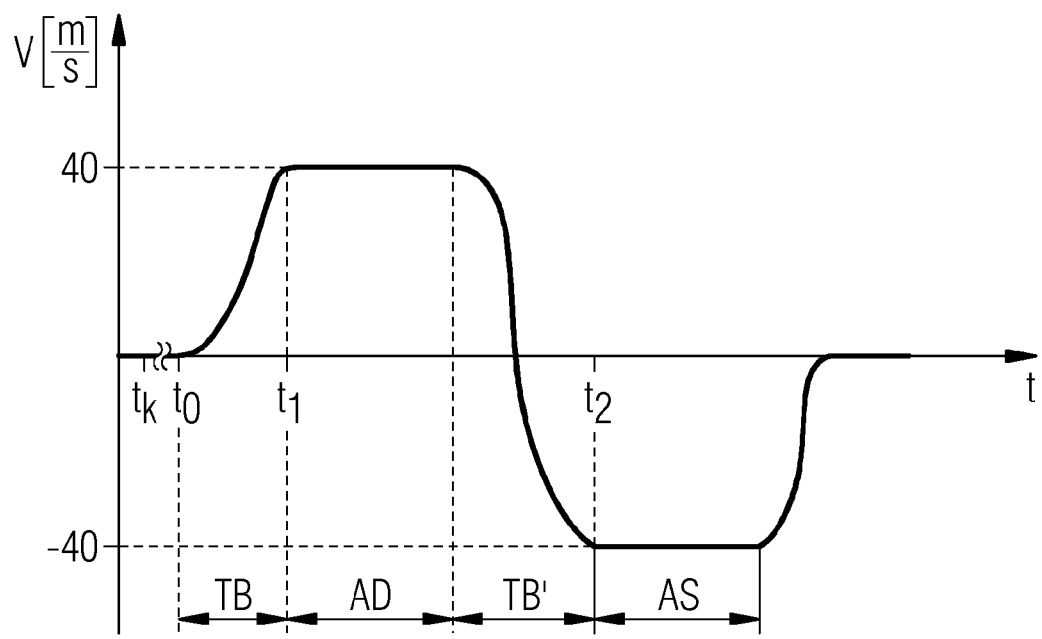
Figure 4:
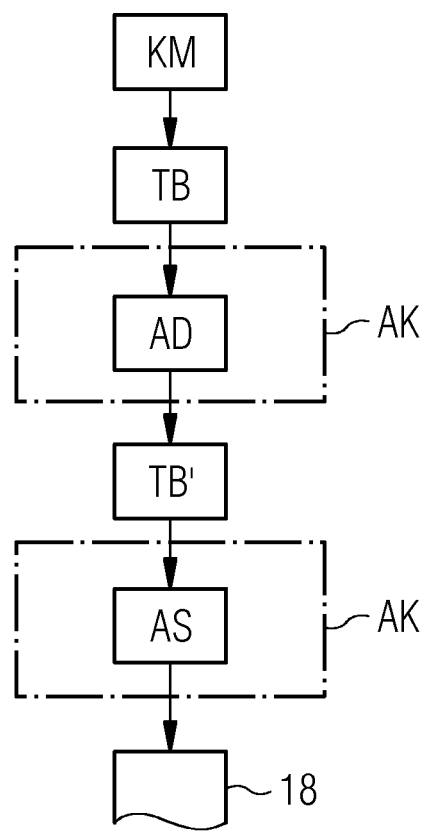

The following now explains the acquisition of projection data 18 for an object under examination 12 with references to FIGS. 2, 3 and 4, wherein here the example used is a contrast medium image of a heart 12.

For this, an EKG signal 56 of the heart 12 shown in FIG. 2 is evaluated, said signal is recorded on the patient 16 by a conventional EKG device (not shown), which is, for example, connected to the control device 7 by a data link. The EKG signal 56 shown reproduces a cardiac cycle 52 which the beating heart 12 undergoes continuously periodically in a simplified representation. The cardiac cycle 52 encompasses a systolic phase 36 beginning, for example, with a so-called "R wave" 54 and the subsequent diastolic phase 38.

Before the start of the acquisition AK (see FIG. 4) of the projection data 18, the EKG signal 56 is evaluated over lengthy period to ensure that the cardiac rhythm is regular and hence the cardiac cycle 52 can be predicted as well as possible within certain limits.

If there is a regular cardiac rhythm or the cardiac rhythm can be adequately predicted, for example by trend analyses, the imaging time points t1, t2 (see FIG. 2) for the acquisition AK of the projection data 18, are determined, for example, by the control device 7. For this, the cardiac rhythm is evaluated and, together with the time for the dispersal of the contrast medium, a speed profile is determined for the patient's bench 8 in order to ensure that, following the administration of a contrast medium KM (see FIG. 4) at time point tk (see FIG. 2), during the imaging time points t1, t2, the heart 12 is located in the measuring field of the tube/detector systems 42, 44. FIG. 2 only shows two imaging time points t1, t2 in different cardiac phases. Each of these imaging time points t1, t2 represents a plurality of closely adjacent imaging time points at each of which sufficient projection data 18 are accepted for the reconstruction of the image data of the complete heart in this cardiac phase.

Usually, a contrast medium KM is administered in a first step 40 s to 50 s before the first projection data 18 are acquired. The acquisition AK of the projection data 18 is then performed as described below in two partial steps in a so-called high-pitch-spiral method with a table speed of 45 cm/s and a pitch of 3.4. For this, the two X-ray tubes of the two tube/detector systems 42, 44 are operated with the same X-ray voltage in order to accelerate the recording time and obtain optimum time resolution. Since scanning speeds of up to up to 450 mm/s can be achieved in this way, it is also possible to produce "snapshots" of fast-moving organs like a heart. Recording methods of this kind also permit very low-dose images, in particular of the coronary vessels. For example, corresponding measurements only require a dose of about 1 mSv.

For this, for example, after the detection of an R wave 54 of the EKG 56 at time point t0 in a second step in an acceleration phase TB (see FIG. 4), the patient's bench 8 is accelerated in the direction I along the system axis 9 (see FIG. 1) until it has reached a speed of 40 cm/s (see FIG. 3).

Here, the acceleration phase TB is selected such that, at the time of a diastolic phase 38 the heart 12 is located in the measuring field of the tube/detector systems 42, 44 and all the projection data for the acquisition of the heart volume are acquired in this phase 38 in a step "scanning the diastole" AD during a first cardiac cycle 52. Due to the fast optimized scan method, this step only lasts about 200-250 ms. Nevertheless, this entails a plurality of individual measuring time points in short succession, which are represented in the diagrams by one individual time point t1, for example the start-time point, of the measurement.

When the heart has been completely acquired in the diastolic phase 38, in a reciprocal acceleration phase TB', the patient's bench 8 is stopped and accelerated in a direction of movement opposing the direction I along the system axis 9 until it has again reached the measuring velocity of 40 cm/s. HereHereHerehHere, braking and re-acceleration is performed so that the table is located relative to the scanner with the correct speed at the correct time so that the heart 12 is located in the measuring field of the tube/detector systems 42, 44 during the systolic phase 36 and a further recording of the complete heart can be performed. This is then followed by the step "scanning the systole" AS at time point t2 (see FIG. 4), wherein here, once again, the entire time interval, which is made up of a plurality of individual measuring time points, is only represented by one time point t2.

FIG. 3 is a simplified diagram of a speed profile of the patient's bench during the entire measuring sequence of these two sequential measurements. In order to adapt the speed profile to the cardiac phases between the two measurements, in the simplest case, a pause matched to the cardiac cycle is calculated and inserted between the two measurements before the table's return journey. However, preferably, there is a dynamic adaptation of the length of the distance traversed by the table so that there is no pause in movement and the patient experiences a pleasant oscillating movement of the table. This oscillating movement also avoids additional motion artifacts, since backward movements are avoided. The total course of the measurement is performed, as described above, a priori on the basis of a prediction of the EKG signals. Alternatively, the process described can also be arranged dynamically or optimized in real time taking into account the current EKG signal.

The measurements in the two cardiac phases can, for example, be performed with a Somatom Definition Flash made by the company Siemens using the afore-described method in a time window of only about 6 s thus permitting the use of a normal injection protocol.

Hence, the two acquisition steps AK result in projection data 18, which were accepted at different imaging time points t1, t2 during different cardiac phases 36, 38, wherein the first imaging time point t1 is in the diastolic phase 38 of the heart 12 while the second imaging time point t2 is in the systolic phase 36.

It is clear that the method can also be performed such that recording takes place first in the systolic phase and then in the diastolic phase. For example, the desired cardiac phase can be determined individually at a user interface for each scan and also a number of possible repetitions established. The calculation of the optimum distance to be traversed by the table or the required pauses is adapted accordingly.

Figure 5:
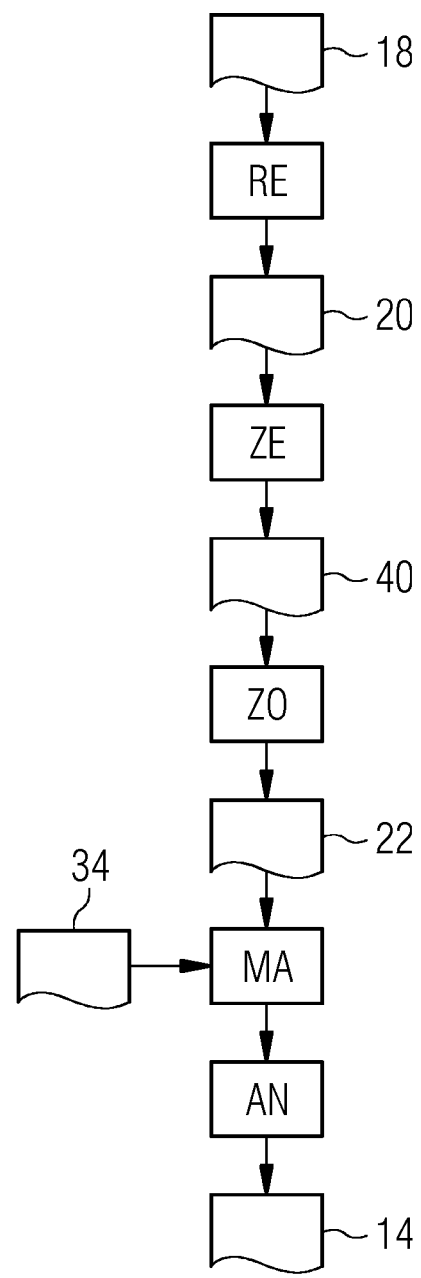

There now follows an explanation of the process for the creation of a 4D image data record 14 on the basis of the projection data 18 with reference to FIG. 5.

In a first step, the projection data 18 are subjected to reconstruction RE. A reconstruction RE of this kind is familiar to the person skilled in the art and will, therefore, not be further described here.

The reconstruction RE results in volume image data 20. These image data 20 are stored in the memory unit 24 of the image processing device 10 (see FIG. 1).

The image data 20 represent so-to-speak 3D snapshots of a beating heart 12 recorded in the two cardiac phases 36, 38. However, since the acquisition of the projection data 18 at the two imaging time points t1, t2 requires a certain measuring period, strictly speaking, the image data 20 contain a plurality of spatially different image sections which were acquired during the measuring period at different measuring time points.

In a further step "dissection" ZE, the image data 20 are, for example, dissected into individual slice images and the dissected image data 40 are then, in an assignment step ZO, each assigned to exact specific imaging time points at which the projection data were acquired, which were used for the reconstruction of the slice image in question. This assignment of the dissected image data 40 to the imaging time points is used to form a space/time data record 22. Here, the time points are each given relative to a reference time point within the cardiac cycle regardless of which cardiac cycle the respective image was recorded in.

In a further step "model selection" MA, a suitable parameterized 4D image data model 34 is selected, which describes the internal and external contours of the heart 12 during an entire cardiac cycle 52 or over several cardiac cycles. Here, a 4D image data model encompasses a plurality of 3D data records 58 of a heart 12, which are arranged temporally one behind the other and, when reproduced on a display, would give the observer the impression of a beating heart 12. FIG. 6 is a schematic depiction of a 3D image data model 34 of this kind in the form of a plurality of 4D data records 58 over a time axis t. Hence, the 4D image data model 34 is a type of "normal film" of a standardized heart 12, wherein different 4D image data models are available for selection for different patient types.

In a subsequent adaptation step AN, the 4D image data model 34 is adapted to the space/time data record 22 in order to generate an individual 4D image data record 14 for the current object under examination 12, from which the space/time data record 22 originates. For this, as shown schematically in FIG. 6, the data in the space/time data record 22 is used so-to-speak as support points in order to set the variable parameters of the parameterized 4D image data model 34 in such a way that, at the temporal positions at which image data of the space/time data record 22 are present, the 3D image data records 58' are adapted as well as possible to these image data. The result is then an individualized 4D image data model or an individual 4D image data record 14 for the heart under examination 12.

The use of the 4D image data record 14 generated is this way then enables functional information to be obtained on the heart currently under examination by way of an analysis of the heart movements. For example, an analysis of the shape and volume change of the myocardium of the left and right ventricle enables information to be obtained on the ejection fraction, the mass of the myocardium, etc. The internal and external contours of the heart over time are also known. The data or parameters derived therefrom are then reproduced, for example, in the conventional way as a polar plot, for example as a 12-segment presentation.

The above measurements relate to an acquisition of the diastolic phase and the systolic phase after the administration of a contrast medium. Both measurements can be performed with a high-pitch spiral scan with a relatively low dose of about only about 1 mSv each. Preferably, additionally, for a virtually complete heart examination, a further high-pitch spiral scan is performed in the diastolic phase without contrast medium (native measurement). This measurement can be performed with an even lower dose of only about 0.3 mSv.

These three measurements make the following evaluations possible:

The plain measurement permits the evaluation and diagnosis of coronary, valvular and aortic calcification.

The contrast medium measurement in the diastolic phase permits the evaluation and diagnosis of the coronary vessels and surrounding organs.

A combination of the plain measurement and the diastolic contrast medium measurement enables the so-called "first-pass-enhancement myocardial perfusion" to be analyzed. This can achieve a quality comparable with that of a dual-energy-measurement, but with a much lower dose.

The creation according to at least one embodiment of the invention of an individual 4D image data record 14 on the basis of the diastolic and the systolic measurement enable all necessary functional evaluations to be performed.

Overall, therefore, the method according to at least one embodiment of the invention with a dose of less than 3 mSv enables virtually the same information to be obtained as with conventional methods used hitherto with more than 10 mSv.

Optionally, it is possible to perform still further additional measurements each requiring a dose of only about 1 mSv.

For example, it is possible, without the further administration of a contrast medium, after a waiting time, for a further scan to be performed in the diastolic phase in order to perform of the so-called "late enhancement" of the myocardium (rest or stress). For this, the plain measurement (after suitable elastic registration of the image data for the reduction of motion artifacts) for the calibration of the myocardial image of the "late enhancement myocardial perfusion" from this additional measurement is used. This enables a comparable quality to be obtained as with a dual-energy-measurement with extracted iodine and plain images, but, once again, with a much lower dose.

In addition, it is possible with a further administration of a contrast medium also to perform a measurement of the diastolic phase under stress in order in this way to permit a so-called rest-stress analysis of the cardiac muscle. Here, after a corresponding registration, the plain measurement is also used to calibrate the myocardial image from this additional stress measurement. Once again, this measurement is able to achieve a comparable quality as that obtained with a dual-energy-measurement with extracted iodine and plain images, but with a much lower dose.

Finally, attention is again drawn to the fact that the method and apparatuses described above only relate to preferred example embodiments of the invention and that the invention can be varied by the person skilled in the art without leaving the scope of the invention as long as it is disclosed in the claims. For purposes of completeness, reference is also made to the fact that the use of the indefinite article "a" or "an" does not exclude the possibility that the features in question could also occur several times.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, comprising:
   reconstructing image data of a heart under examination, the reconstructing being based upon projection data previously acquired by helical scans of a computed tomography system, the projection data being acquired at different imaging time points, and linking the reconstructed image data with the imaging time points to a space/time data record, the space/time data record being formed by dissecting the reconstructed image data into individual slice images and assigning the individual slice images to respective ones of the different imaging time points; and
   adapting a parameterized 4D image data model to the space/time data record by varying at least one parameter of the 4D image data model.

2. The method as claimed in claim 1, wherein the different imaging time points comprise a plurality of time points within at least two spaced-apart movement phases of the heart under examination.

3. The method as claimed in claim 2, wherein the different imaging time points comprise a plurality of time points within at least a systolic phase and a diastolic phase of a heart.

4. A method for determining at least one of structural and functional data of a heart under examination, based on a computed tomography measurement, comprising:
   using the method as claimed in claim 1 to generate a 4D image data record of the heart under examination; and
   analyzing the 4D image data record with respect to the at least one of structural and functional data.

5. A non-transitory computer readable medium including program segments for, when executed on a computer device, causing the computer device to implement the method of claim 4.

6. A non-transitory computer readable medium including program code sections to carry out the method according to claim 1 when the program code sections are executed by a processor.

7. A non-transitory computer readable medium including program segments for, when executed on a computer device, causing the computer device to implement the method of claim 1.

8. The method as claimed in claim 1, wherein the helical scans include a first scan of a first phase of the heart, a second scan of a second phase of the heart, and a third scan of the first phase of the heart, and wherein the first and second scans are performed while a contrast agent is present in the heart and the third scan is performed without a contrast agent being present in the heart.

9. The method as claimed in claim 8, wherein the first phase is a diastolic phase and the second phase is a systolic phase.

10. The method as claimed in claim 8, wherein the first, second, and third scans are performed with less than a dose of 3 mSv.

11. The method as claimed in claim 1, wherein the different imaging time points comprise a plurality of time points within at least a diastolic phase and a systolic phase of a same cardiac cycle of the heart under examination.

12. The method as claimed in claim 1, wherein the reconstructing reconstructs a complete 3D image data volume before the space/time data record is formed.

13. A method for obtaining a 4D image data record of a heart under examination using a computed tomography system, comprising:
   acquiring projection data, at different imaging time points, via a helical scan method using a computed tomography system;
   reconstructing, on the basis of the projection data, image data of the heart under examination and correcting the reconstructed image data by linking the reconstructed image data with the imaging time points to a space/time data record, the space/time data record being formed by dissecting the reconstructed image data into individual slice images and assigning the individual slice images to respective ones of the different imaging time points; and
   individualizing, on the basis of the reconstructed image data, a 4D image data model adapted from the space/time data record by varying at least one parameter of the 4D image data model.

14. The method as claimed in claim 13, wherein at least the projection data recorded within a movement phase of the heart under examination at different imaging time points are acquired within a movement cycle of the heart under examination.

15. The method according to claim 14, wherein a relative direction of movement of patient's bench of the computed tomography system is reversed between a recording of projection data in a first movement phase of the heart under examination and a recording of projection data in a second movement phase of the heart under examination.

16. The method as claimed in claim 15, wherein, before a start of the acquisition of the projection data, the patient's bench is accelerated relative to a measuring velocity during an acceleration phase.

17. The method as claimed in claim 15, wherein, before a start of the acquisition of the projection data, the patient's bench is accelerated relative to a measuring velocity during an acceleration phase.

18. The method as claimed in claim 13, wherein the computer tomography scanner is a dual source computed tomography scanner with at least two X-ray tubes.

19. The method according to claim 13, wherein a plurality of measurements are performed to obtain a plurality of 4D image data records of the heart under examination using the computed tomography system, for each of the measurements, at different imaging time points, the helical scan method is used to acquire projection data, wherein at least one of the measurements is performed following the administration of a contrast medium to the heart under examination.

20. The method according to claim 13, wherein the heart under examination is moved on a patient's bench of the computed tomography system relative to a projection imaging system of the computed tomography system in dependence on an EKG signal.

21. A method for determining at least one of structural and functional data of a heart under examination, based on a computed tomography measurement, comprising:
   using the method as claimed in claim 13, to generate a 4D image data record of the heart under examination; and
   analyzing the 4D image data record with respect to the at least one of structural and functional data.

22. A non-transitory computer readable medium including program segments for, when executed on a computer device, causing the computer device to implement the method of claim 21.

23. A non-transitory computer readable medium including program segments for, when executed on a computer device, causing the computer device to implement the method of claim 13.

24. An image processing device, comprising:
   an interface configured to accept projection data of a heart under examination, the projection data being acquired via a computed tomography system at different imaging time points using a helical scan method and configured to accept time data containing information on the imaging time points belonging to the projection data;
   a reconstruction device configured to reconstruct image data of the heart under examination on the basis of the projection data and link the reconstructed image data with the imaging time points to a space/time data record, the space/time data record being formed by dissecting the reconstructed image data into individual slice images and assigning the individual slice images to respective ones of the different imaging time points;
   a model interface configured to accept a parameterized 4D image data model; and
   a model individualization device configured to individualize the 4D image data model by varying at least one parameter of the 4D image data model for adaptation to the space/time data record.

25. A computed tomography system comprising:
   at least one X-ray source;
   at least one detector for acquisition of projection data records of a heart under examination; and
   the image processing device as claimed in claim 24.

\* \* \* \* \*